US006602283B2

(12) United States Patent
Doran et al.

(10) Patent No.: US 6,602,283 B2
(45) Date of Patent: *Aug. 5, 2003

(54) STENT DESIGN

(75) Inventors: Burns P. Doran, Albertville, MN (US); Graig L. Kveen, Maple Grove, MN (US); Timothy J. Ley, Shoreview, MN (US)

(73) Assignee: SciMed Life Systems, Inc., Maple Grove, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/681,447

(22) Filed: Apr. 6, 2001

(65) Prior Publication Data

US 2002/0147493 A1 Oct. 10, 2002

(51) Int. Cl.[7] .................................................. A61F 2/06
(52) U.S. Cl. ..................................................... 623/1.15
(58) Field of Search .............................. 623/1.11, 1.12, 623/1.13, 1.14, 1.15, 1.16, 1.17, 1.18, 1.19, 1.2; 606/191, 193, 194, 198

(56) References Cited

U.S. PATENT DOCUMENTS

| | | | | |
|---|---|---|---|---|
| 5,697,971 A | | 12/1997 | Fischell et al. ................. 623/1 |
| 5,861,027 A | * | 1/1999 | Trapp .......................... 606/191 |
| 5,876,449 A | * | 3/1999 | Starck et al. ............... 623/23.7 |
| 5,911,754 A | | 6/1999 | Kanesaka et al. ............... 623/1 |
| 5,913,895 A | | 6/1999 | Burpee et al. .................. 623/1 |
| 5,935,162 A | * | 8/1999 | Dang ............................ 623/1 |
| 6,015,433 A | * | 1/2000 | Roth .......................... 623/1.15 |
| 6,033,433 A | | 3/2000 | Ehr et al. ....................... 623/1 |
| 6,042,597 A | * | 3/2000 | Kveen et al. ............... 623/1.15 |
| 6,083,259 A | | 7/2000 | Frantzen .................... 623/1.15 |
| 6,117,165 A | | 9/2000 | Becker ........................... 623/1 |
| 6,190,403 B1 | * | 2/2001 | Fischell et al. ............ 623/1.16 |
| 6,190,405 B1 | * | 2/2001 | Culombo et al. .......... 623/1.15 |
| 6,258,116 B1 | * | 7/2001 | Hojeibane ................. 623/1.16 |

FOREIGN PATENT DOCUMENTS

| | | |
|---|---|---|
| WO | 96/26689 | 9/1996 |
| WO | 98/26732 | 6/1998 |
| WO | 00/42946 | 7/2000 |

* cited by examiner

Primary Examiner—Kevin T. Troung
Assistant Examiner—Vy Q. Bui
(74) Attorney, Agent, or Firm—Vidas, Arrett & Steinkraus

(57) ABSTRACT

A stent comprises at least one band of interconnected cells selected from the group consisting of S-shaped cells and mirror image S-shaped cells. Each cell has a top end and a bottom end. The top end of each cell is attached to the bottom end of an adjacent cell in the band. Adjacent bands may abut one another or may be joined by connecting members.

15 Claims, 4 Drawing Sheets

STENT DESIGN

BACKGROUND OF INVENTION

A stent is a structure which is designed to maintain the patency of a bodily vessel. Stents are delivered to a desired bodily location in an unexpanded configuration having a reduced cross-section and expanded to a configuration having an increased cross-section. Stents are typically self-expandable or mechanically expandable. Examples of self-expandable and mechanically expandable stents are disclosed in WO 9626689 and U.S. Pat. No. 6,042,597.

It is desirable for a stent to be flexible in the unexpanded configuration to facilitate delivery of the stent through tortuous vessels and to have a sufficient degree of rigidity in the expanded configuration to support a vessel. It is also desirable for a stent in the expanded configuration to provide sufficient vessel coverage.

Although a vast number of stent designs have been disclosed in recent years, there remains a need for innovative stent designs which are flexible in the unexpanded configuration and which exhibit improved coverage characteristics in the expanded configuration. There also remains a need for stents with improved expansion ratios relative to current stents.

All U.S. patents and applications and all other published documents mentioned anywhere in this application are incorporated herein by reference in their entirety.

The invention in various of its embodiment is summarized below. Additional details of the invention and/or additional embodiments of the invention may be found in the Detailed Description of the Invention below.

SUMMARY OF INVENTION

In one embodiment, the invention is directed to a stent comprising at least one band of interconnected cells selected from the group consisting of circumferentially oriented S-shaped cells and circumferentially oriented mirror image S-shaped cells. Each cell has a top end and a bottom end. The top end of each cell is attached to the bottom end of an adjacent cell in the band. The stent may comprise a plurality of interconnected bands of interconnected S-shaped cells and/or mirror image S-shaped cells. Where bands of S-shaped cells and bands of mirror image S-shaped cells are present, the bands may alternate over the length of the stent or be provided in any other suitable arrangement. Adjacent bands of S-shaped cells and/or mirror image S-shaped cells may abut one another or may be joined by connecting members. Where connecting members are provided, the members may be straight or may have one or more bends therein. The stent may have a single type of connecting member or multiple types of connecting members. Adjacent connecting members may be joined to one another to form differently shaped cells. In one embodiment, the differently shaped cells are generally arrow shaped.

The invention is also directed to a stent comprising at least one cell selected from the group consisting of S-shaped cells and mirror image S-shaped cells.

The invention is also directed to stents comprising at least one band formed of a plurality of substantially X-shaped members. Each X-shaped member has a proximal end and a distal end and includes a first arm of a first length, a second arm of a second length different from the first length, a third arm of a third length and a fourth arm of a fourth length different from the third length. The first and second arms extend in a distal direction and the third and fourth arms extend in a proximal direction. Adjacent X-shaped members are joined together at the distal end by a first loop member extending there between and at the proximal end by a second loop member extending therebetween. The first loop member and the second loop are non-parallel to the longitudinal axis of the stent. The first loop member includes a first loop oriented substantially in the proximal direction and a second loop oriented substantially in the distal direction and the second loop member includes a first loop oriented substantially in the proximal direction and a second loop oriented substantially in the distal direction. Adjacent bands of substantially X-shaped members may abut one another or may be joined by connecting members extending therebetween. Where connecting members are provided, the members may be straight or may have one or more bends therein. The stent may have a single type of connecting member or multiple types of connecting members. Adjacent connecting members may be joined to one another to form differently shaped cells. In one embodiment, the differently shaped cells are generally arrow shaped.

The invention is also directed to a stent comprising one or more cells with each cell consisting of two inwardly pointing fingers, one of which opens in a proximal direction and the other of which opens in a distal direction. The closed portion of the finger which opens in the distal direction is located proximal of the closed portion of the finger which opens in the distal direction.

DETAILED DESCRIPTION

Figure 1:
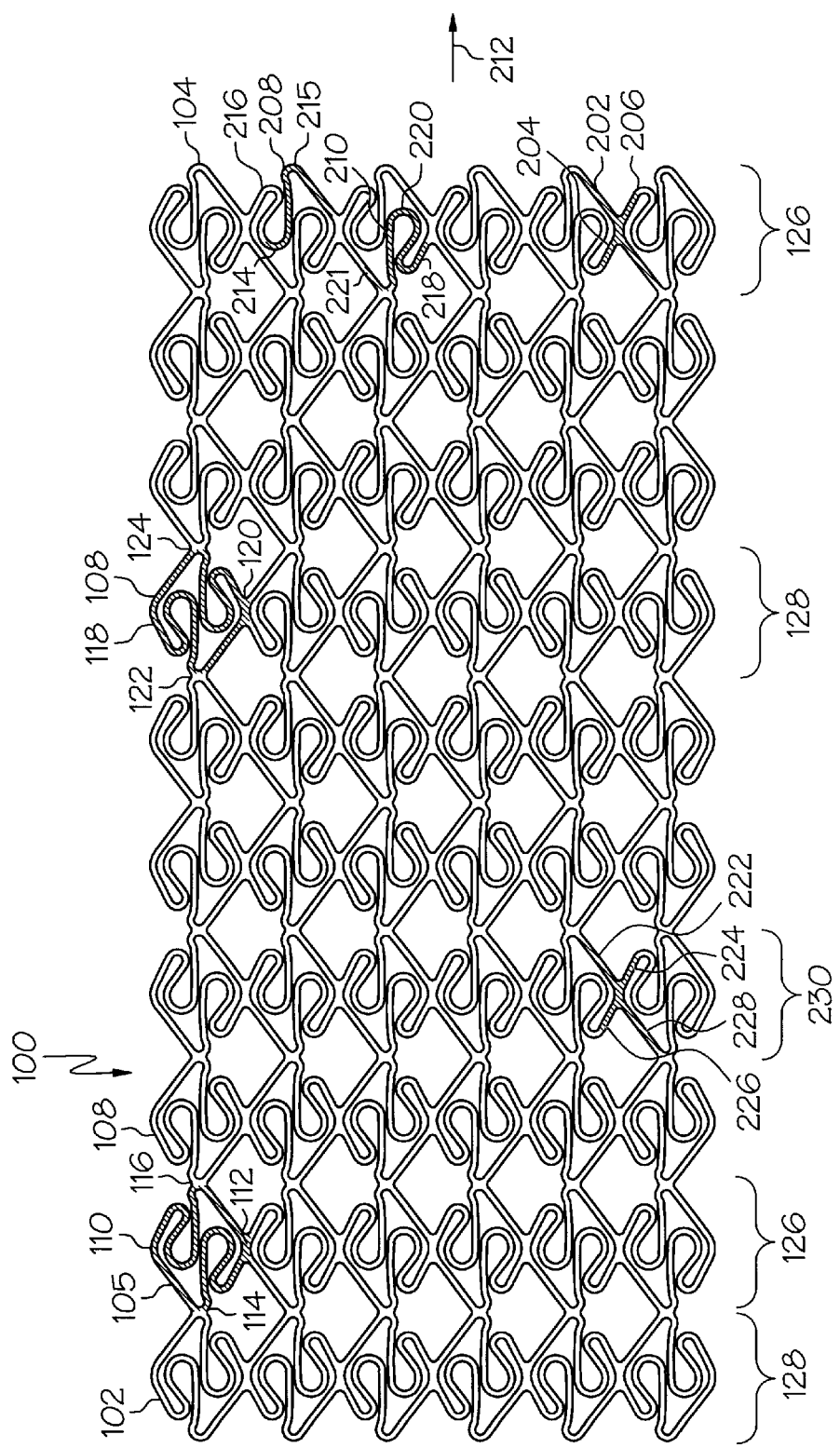
FIG. 1 shows a flat pattern of an embodiment of the inventive stent in an unexpanded configuration.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, unless otherwise indicated, identical reference numerals used in different figures refer to the same component.

FIG. 1 illustrates in flattened form one of the embodiments of the stent of the present invention in an unexpanded configuration. The stent, shown generally at 100 in FIG. 1 has a proximal end 102, a distal end 104 and is composed of a plurality of interconnected circumferentially oriented S-shaped cells 106 (one of which is shown highlighted) and circumferentially oriented mirror image S-shaped cells 108 (one of which is shown highlighted). Th longitudinal axis 212 of the stent corresponds to the direction of flow in the stent. Each S-shaped cell 106 has a top end 110 and a bottom end 112 and a proximal end 114 and a distal end 116. Each mirror image S-shaped cell 103 has a top end 118 and a bottom end 120 and a proximal end 122 and a distal end 124. The S-shaped cells have S-shaped openings therein and the mirror-image S-shaped cells have mirror image S-shaped openings therein.

Adjacent S-shaped cells are connected top-to-bottom with top end 110 of an S-shaped cell abutting bottom end 112 of an adjacent S-shaped cell to form a band 126 of S-shaped cells. Similarly, adjacent mirror image S-shaped cells are connected top-to-bottom with top end 118 of mirror image S-shaped cell 108 abutting bottom end 120 of an adjacent mirror image S-shaped cell to form a band 128 of mirror image S-shaped cells. Bands 126 of S-shaped cells alternate along the length of the stent with bands 128 of mirror image S-shaped cells. Distal ends 116 of S-shaped cells 106 are joined to proximal ends 122 of mirror image S-shaped cells. Similarly, distal ends 124 of mirror image S-shaped cells 108 are joined to proximal ends 114 of S-shaped cells 106.

The stent shown in FIG. 1 terminates on the proximal end 102 in a band 128 of mirror image S-shaped cells 108 and on the distal end 104 in a band 126 of S-shaped cells 106. The invention also contemplates other arrangements as well including embodiments in which the stent terminates in S-shaped cells in the proximal end and mirror image S-shaped cells in the distal end. Moreover, both ends may terminate in a band of S-shaped cells or in a band of mirror image S-shaped cells. The invention further contemplates the possibility of one or more of the ends of the stent terminating in bands other than those containing S-shaped cells or mirror image S-shaped cells.

Figure 2:
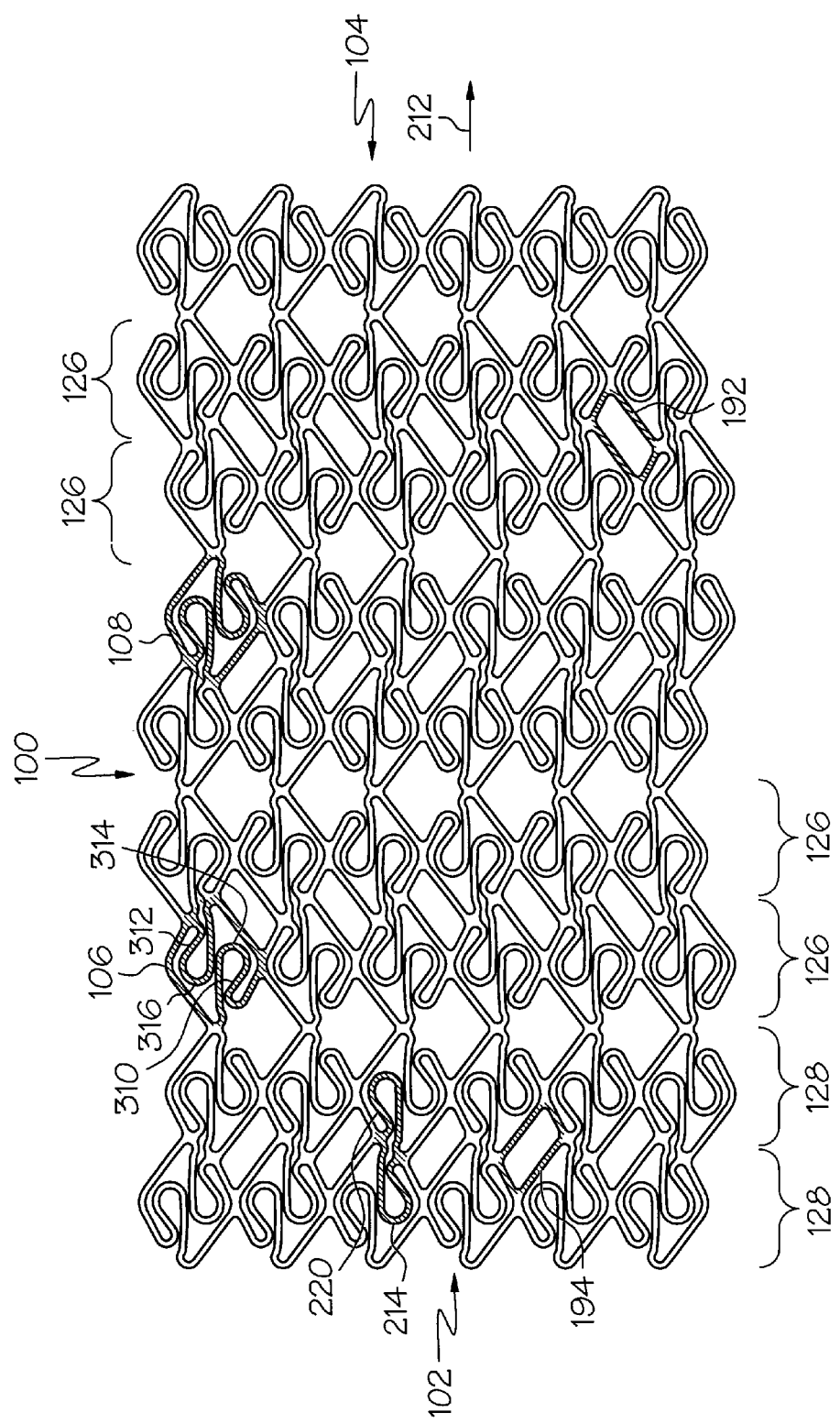
FIG. 2 shows a flat pattern of another embodiment of the inventive stent in an unexpanded configuration.

In the embodiment of FIG. 1, bands of S-shaped cells 126 alternate along the length of the stent with bands 128 of mirror image S-shaped cells. The invention also contemplates inventive stent comprising one or more bands of S-shaped cells and one or more bands of mirror image S-shaped cells where the bands do not alternate with one another over the length of the stent. In the embodiment of FIG. 2, for example, with the exception of distal end 104 of stent 100, S-shaped cells 126 are provided in groupings of two and mirror image S-shaped cells 128 are provided in groupings of two, which alternate with one another over the length of stent. The stent of FIG. 2 may also be modified to provide a grouping of two mirror image S-shaped cells at the distal end of the stent. Other modification include replacing the S-shaped cells with mirror image S-shaped cells and replacing mirror image S-shaped cells with S-shaped cells. Further in accordance with the invention, the bands of S-shaped cells and/or the bands of mirror image S-shaped cells may be provided in groups of three, four or more bands.

Where bands of S-shaped cells abut one another, substantially parallelogram shaped first openings 192 are formed between adjacent bands of S-shaped cells. Similarly, bands of mirror image S-shaped cells abut one another, substantially parallelogram shaped second openings 194 are formed between adjacent bands of mirror image S-shaped cells. The orientation of substantially parallelogram shaped first and second openings are opposite one another.

The invention is also directed to a stents, such as that shown for example in FIG. 2, comprising cells with substantially polygonal shaped first openings 192 extending in a first direction, where circumferentially adjacent cells having substantially polygonal shaped first openings are joined by one or more looped portions 214. Desirably, as shown in FIG. 2, circumferentially adjacent cells having substantially polygonal shaped first openings 192 are joined by at least two looped portions 214 and 220 which generally open toward one another. As shown in FIG. 2, the substantially polygonal shaped first openings are in the form of parallelograms. Cells with other substantially polygonal openings including triangular opening, pentagonal openings and hexagonal openings may be used in other embodiments of the invention.

Optionally, as shown in FIG. 2, the stent may include cells with openings 192 which extend in a first oblique direction relative to the longitudinal axis of the stent and cells with openings 194 which extend in a second oblique direction relative to the longitudinal axis of the stent. Desirably, the first and second oblique directions are opposite one another.

The inventive stent may also be made exclusively of one or more bands of S-shaped cells or exclusively of one or more bands of mirror image S-shaped cells.

Figure 3:
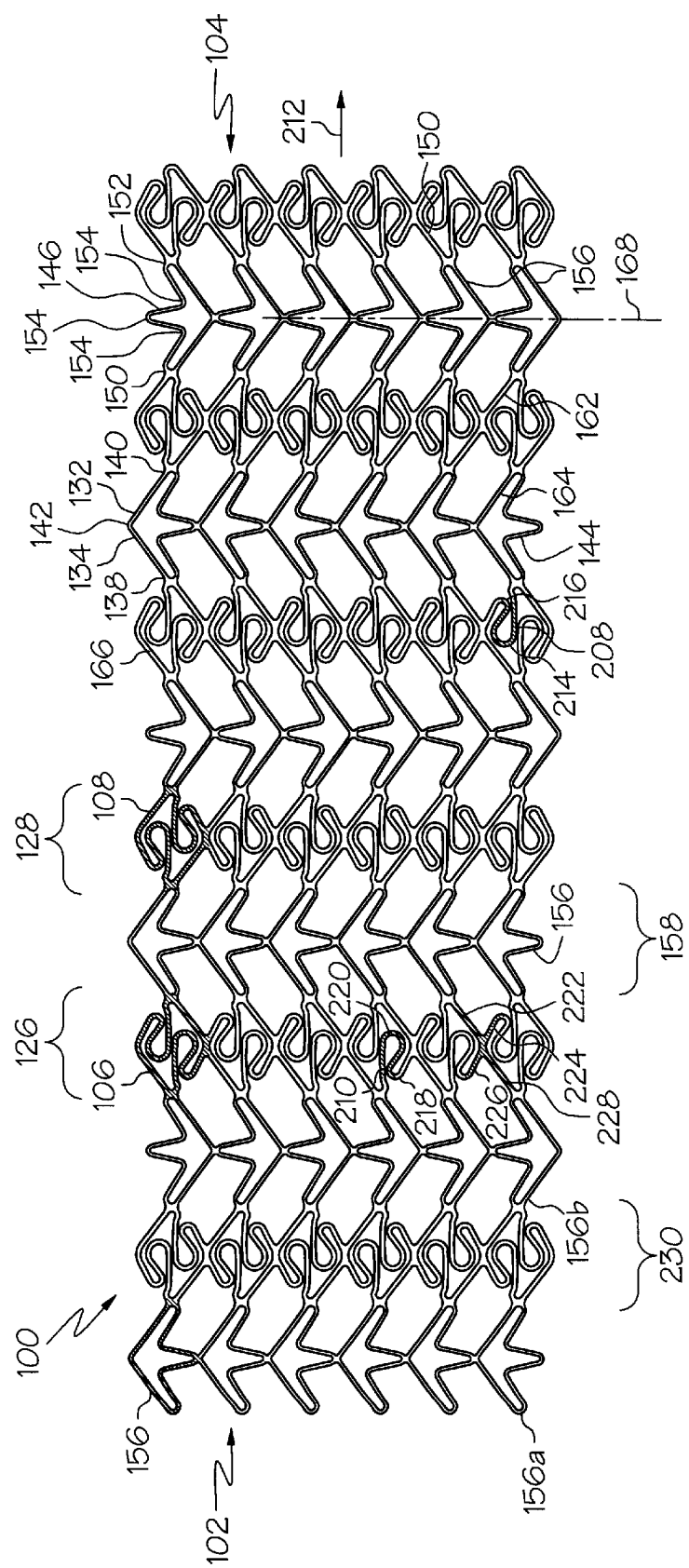
FIG. 3 shows a flat pattern of another embodiment of the inventive stent in an unexpanded configuration.

The invention also contemplates providing interconnecting elements between adjacent bands of S-shaped cells and/or mirror image S-shaped cells. The unexpanded stent of FIG. 3, shown generally at 100 in FIG. 3 in a flat pattern, comprises alternating bands 126 of S-shaped cells 106 and bands 128 of mirror image S-shaped cells 108. The longitudinal axis 212 of the stent corresponds to the direction of flow in the stent. Extending between adjacent bands are first connecting members 132 and second connecting members 144.

First connecting members 132 have a proximal end 138, a distal end 140, a middle portion 134 therebetween and a single bend 142 between proximal end 138 and distal end 140. As the stent is traversed from the proximal end to the distal end, first connecting members 132 extend from the distal ends of S-shaped cells (and mirror image S-shaped cells) to the proximal ends of adjacent S-shaped cells (and mirror image S-shaped cells).

Second connecting members 144 have a proximal end 150, a distal end 152, a middle portion 146 therebetween and three bends 154 between proximal end 150 and distal end 152. As the stent is traversed from the proximal end to the distal end, second connecting members 144 extend from the distal ends of S-shaped cells (and mirror image S-shaped cells) to the proximal ends of adjacent S-shaped cells (and mirror image S-shaped cells).

Middle portions 134 of first connecting members 132 are connected to middle portions 146 of adjacent second connecting members 144 to form differently shaped cells in the form of arrow cells 156 (one of which is shown highlighted).

In the embodiment of FIG. 3, arrow cells 156 are disposed in bands 158 about the periphery of the stent. The orientation of bands 158 of arrow cells 156 alternates along the length of the stent. Arrow cells 156a are oriented in a first circumferential direction and arrow cells 156b are oriented opposite to arrow cells 156a. The invention also contemplates a stent where the orientation of the arrow cells does not alternate over the length of the stent.

The stent of FIG. 3 is provided with several additional types of cells. Third types of cells 160, fourth types of cells 162, fifth types of cell 164 and sixth types of cell 166 (one of each of which is shown highlighted) are provided bounded by arrow cells on one side and S-shaped cells or mirror image S-shaped cells on the other side. The third, fourth, fifth and sixth types of cells are related to one another via various symmetry operations. For example, fourth type of cell 162 as seen in the flat pattern of FIG. 3, is a mirror image of third type of cell 160 about an axis 168 which bisects arrow cells 156. Fifth type of cell 164 is a mirror image of third type of cell 160 about the longitudinal axis 212 of the stent. Finally, sixth type of cell 166 is a mirror image of fifth type of cell 164 about axis 168.

As shown in FIG. 3, the struts forming first connecting members 132 and second connecting members 144 are not as wide as the struts forming the S-shaped cells and the mirror image S-shaped cells. The invention also contemplates embodiments in which the struts forming the first and second connecting members are as wide as or wider than the struts forming the S-shaped cells and the mirror image S-shaped cells.

Further as shown in FIG. 3, arrow cells 156 are longer in the longitudinal direction than the S-shaped cells and mirror image S-shaped cells. The invention also contemplates embodiments in which the S-shaped cells and mirror image S-shaped cells are of the same longitudinal length or are longer longitudinally than the arrow shaped cells.

Figure 4:
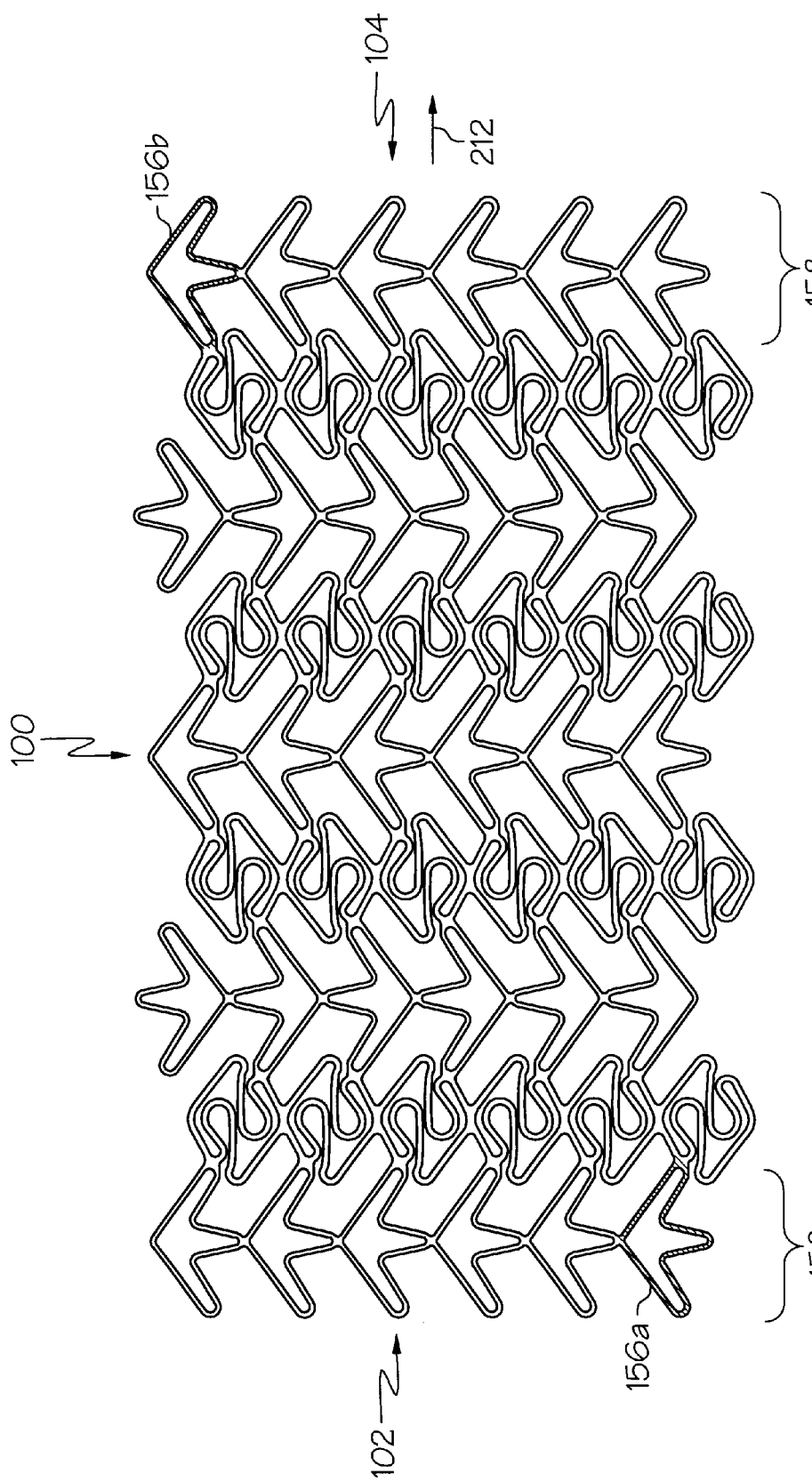
FIG. 4 shows a flat pattern of another embodiment of the inventive stent in an unexpanded configuration.

In the embodiment of FIG. 3, proximal end 102 of stent 100 terminates in band 158 of arrow cells 156, one of which is shown hatched, and distal end 104 of stent 100 terminates in a band 126 of S-shaped cells. It is also within the scope of the invention for both ends of the stent to terminate in a band of arrow cells. As shown in FIG. 4, distal end 104 of stent 100 terminates in a band 158b of arrow cells 156b having an orientation opposite to that of the proximal-most band 158a of arrow cells 156a. In accordance with the invention, where a band of arrow shaped cells is provided at both ends of the stent, the orientation of arrows at both ends of the stent may be identical. It is further within the scope of the invention for both the proximal and distal ends of the stent to terminate in a band of S-shaped cells, a band of mirror image S-shaped cells or a band of S-shaped cells at one end of the stent and a band of mirror image S-shaped cells at the other end of the stent.

The invention further contemplates embodiments in which the number of cells in band varies in various portions of the stent. For example, a stent may be provided having bands consisting of 'N' S-shaped cells and bands consisting of 'N' mirror image S-shaped cells alternating with bands having 'M' arrow cells where 'M' is less than 'N'. A stent may also be provided in which the number of arrow cells 'M' in a band exceeds the number of S-shaped or mirror image S-shaped cells 'N' in a band.

In another embodiment, the invention is directed to stents having properties which vary along the length of the stent. This may be achieved in a stent in which the number of S-shaped cells and/or mirror image S-shaped cells per band increases along the length of the stent. This may also be achieved in a stent where both ends have more S-shaped cells and/or mirror image S-shaped cells than the middle section of the stent or in a stent where the ends have fewer S-shaped cells and/or mirror image S-shaped cells than the middle of the stent. Other embodiments that are within the scope of the invention include embodiments in which the length and or the width and/or the aspect ratio of the S-shaped cells and/or mirror image S-shaped cells is varied over the length of the stent.

The invention is also directed to stents having bands of S-shaped cells and/or mirror image S-shaped cells joined together with any other type of connecting member. Connecting members of a different length and/or with bends of a different geometry may be provided. Adjacent connecting members may be of different lengths as shown in FIG. 2 or may be of the same length. The connecting members may also be straight.

More generally, the invention is also directed to stents having at least one S-shaped cell and/or at least one mirror image S-shaped cell. Where a plurality of such cells is present, the cells may abut one another or may be spaced apart in the stent. As discussed above, the cells may be provided in one or more interconnected bands. Each band may consist of a single type of cell, whether S-shaped or mirror image S-shaped, or may consist of both S-shaped cells and mirror image S-shaped cells.

The invention is also directed to stents comprising at least one band, formed of a plurality of substantially X-shaped members. As shown in FIG. 1, each X-shaped member 202 has a proximal end 204 and a distal end 206. Adjacent X-shaped members 202 are joined together at distal end 206 by a first loop member 208 extending therebetween and at proximal end 204 by a second loop member 210 extending therebetween. First loop member 208 and second loop member 210 are non-parallel to the longitudinal axis 212 of the stent.

First loop member 208 includes a first loop 214 oriented substantially in the proximal direction, a second loop 216 oriented substantially in the distal direction and a third loop 215 oriented substantially in the distal direction. The shape of the first, second and third loops forming the first loop member differ from one another with first loop 214 having a more bulbous shape than second loop 216 and third loop 215. First and second loops having other geometries as well may also be provided.

Second loop member 210 includes a first loop 218 oriented substantially in the proximal direction, a second loop 220 oriented substantially in the distal direction and a third loop 221 oriented substantially in the proximal direction. The shape of the first second and third loops forming the second loop member differ from one another with second loop 220 having a more bulbous shape than first loop 218 and third loop 221. First and second loops having other geometries as well may also be provided.

Each X-shaped member 202 includes first arm 222 of a first length, second arm 224 of second length different from the first length, third arm 226 of a third length and fourth arm 228 of a fourth length different from the third length. First 222 and second arm 224 extend in a distal direction and third arm 226 and fourth arm 228 extend in a proximal direction.

The inventive stent may have one or more bands 230 formed of one or more substantially X-shaped members 202. As shown in FIG. 1, adjacent bands 230 formed of a plurality of substantially X-shaped members may abut one another. As shown in FIG. 3, the invention is also directed to stents where adjacent bands 230 formed of substantially X-shaped members 202 may be joined by connecting members extending therebetween. A single type of connecting member may join adjacent bands of X-shaped members (not shown) or a plurality of types of connecting members may join adjacent bands. The stent of FIG. 3 is provided with first connecting members 132 and second connecting members 144 extending between adjacent bands 230. As discussed above, first connecting member 132 has a single bend therein and second connecting member 144 has three bends therein. Other shaped connecting members may also be provided.

The invention is also directed to stents in partially expanded and fully expanded configurations having structures such as those shown in FIGS. 1–4.

The invention is also directed to a stent comprising one or more cells with each cell consisting of two inwardly pointing fingers, one of which opens in a proximal direction and the other of which opens in a distal direction. The closed portion of the finger which opens in the distal direction is located proximal of the closed portion of the finger which opens in the distal direction. An example of such an embodiment is shown in FIG. 2. Cell 106 comprises a first inwardly pointing finger 310 and a second inwardly pointing finger 312. Finger 310 opens in a proximal direction and finger 312 opens in a distal direction. Closed portion 316 of finger 312 is located proximal of closed portion 314 of finger 310.

The inventive stents disclosed herein may be self-expanding or mechanically expandable (including balloon expandable). They may be made of any suitable material including metal or polymeric material. Suitable metals include stainless steel, titanium, gold and shape memory materials such as nitinol. The stents may be formed of more than one metal and may include various radiopaque coatings such as a thin layer of gold or other radiopaque metal. Other biocompatible coatings may be provided as well including lubricious coatings as are known in the art.

The stents may be laser cut, chemically etched, electro-discharge machined or cut using any other suitable technique from a tube. The stent pattern may also be cut into a sheet using any of the above-mentioned techniques and the sheet rolled into tubular form and the ends welded or otherwise joined together. The inventive stent designs may also be used in coiled sheet stents where the sheet which forms the stent is formed into a roll which may unroll to a wider opening.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below (e.g. claim 3 may be taken as alternatively dependent from claim 1; claim 5 may be taken as alternatively dependent on claim 3; claim 6 may be taken as alternatively dependent from claim 4 or claim 5; etc.).

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A stent comprising at least one band of interconnected cells selected from the group consisting of cells having circumferentially oriented S shaped openings and cells having circumferentially oriented mirror image S shaped openings, each cell having a top end and a bottom end, the top end of each cell attached to the bottom end of an adjacent cell in the band, the stent including at least one cell with an S shaped opening and at least one cell with a mirror image S shaped opening, the stent configured such that an axis exists about which the cell with the S shaped opening when rotated 1800 is superimposed upon a cell having a mirror image S shaped opening.

2. The stent of claim 1 comprising a plurality of interconnected bands of interconnected cells having S-shaped openings.

3. The stent of claim 2 further comprising a plurality of bands of interconnected cells having mirror image S-shaped openings.

4. The stent of claim 3 wherein the bands of interconnected cells having S-shape openings alternate with the bands of interconnected cells having mirror image S-shaped openings over the length of the stent.

5. The stent of claim 4 wherein adjacent bands of interconnected cells having S-shaped openings and interconnected cells having mirror image S-shaped openings abut one another.

6. The stern of claim 4 wherein adjacent bands of interconnected cells having S-shaped openings and interconnected cells having mirror image S-shaped openings have connecting members extending therebetween.

7. The stent of claim 6 wherein the connecting members have at least one bend therein.

8. The stent of claim 4 wherein adjacent bands of interconnected cells having S-shaped openings and interconnected cells having mirror image S-shaped openings have first connecting members of a first length and second connecting members of a second length different from the first length extending therebetween.

9. The stent of claim 8 wherein each first connecting member is connected to an adjacent second connecting member.

10. The stent of claim 4 wherein adjacent bands of interconnected cells having S-shaped openings and bands of interconnected cells having mirror image S-shaped openings have bands of differently shaped cells therebetween, the differently shaped cells differing in shape from the cells having S-shaped openings and from the cells having mirror image S-shaped openings.

11. The stent of claim 10 wherein the differently shaped cells are in the shape of an arrow.

12. The stent of claim 11 wherein the arrows are oriented in a circumferential direction.

13. The stent of claim 12 wherein adjacent bands of differently shaped cells are oriented in opposing circumferential directions.

14. The stent of claim 3 consisting only of bands of interconnected cells having S-shaped openings and bands of interconnected cells having mirror image S-shaped openings.

15. A stent comprising at least one cell selected from the group consisting of circumferentially oriented cells having S-shaped openings and circumferentially oriented cells having mirror image S-shaped openings, the stent including at least one cell with an S shaped openings and at least on cell with a mirror image S shaped opening, the stent configured such that an axis exists about which the cell with the S-shaped opening when rotated 180° is superimposed upon a cell having a mirror image S-shaped opening.

* * * * *